United States Patent [19]

Shapiro et al.

[11] Patent Number: 5,266,687
[45] Date of Patent: * Nov. 30, 1993

[54] INHIBITORS OF ANGIOGENIN

[75] Inventors: Robert Shapiro, Holliston; Bert L. Vallee, Brookline, both of Mass.

[73] Assignee: The President and Fellows of Harvard College, Cambridge, Mass.

[*] Notice: The portion of the term of this patent subsequent to Oct. 30, 2007 has been disclaimed.

[21] Appl. No.: 701,478

[22] Filed: May 16, 1991

Related U.S. Application Data

[63] Continuation of Ser. No. 177,942, Apr. 5, 1988, Pat. No. 5,019,566, which is a continuation-in-part of Ser. No. 38,008, Apr. 14, 1987, Pat. No. 4,966,964, which is a continuation-in-part of Ser. No. 38,250, Apr. 14, 1987, abandoned.

[51] Int. Cl.[5] .............. C12N 15/00; C12N 9/22; C07K 7/00
[52] U.S. Cl. .................. 536/23.1; 530/328; 530/327; 435/199
[58] Field of Search .............. 536/23.1; 530/328, 327; 435/199

*Primary Examiner*—Robert A. Wax
*Assistant Examiner*—Keith Hendricks
*Attorney, Agent, or Firm*—Allegretti & Witcoff, Ltd.

[57] ABSTRACT

An inhibitor of angiogenin and method of use of the inhibitor, wherein the inhibitor inhibits the angiogenic activity of angiogenin. The inhibitor is dispensed at a suitable concentration within a physiologically compatable medium, suitable for administration to an animal in sufficient quantity to inhibit the biological activity of naturally occurring angiogenin within the animal.

1 Claim, 8 Drawing Sheets

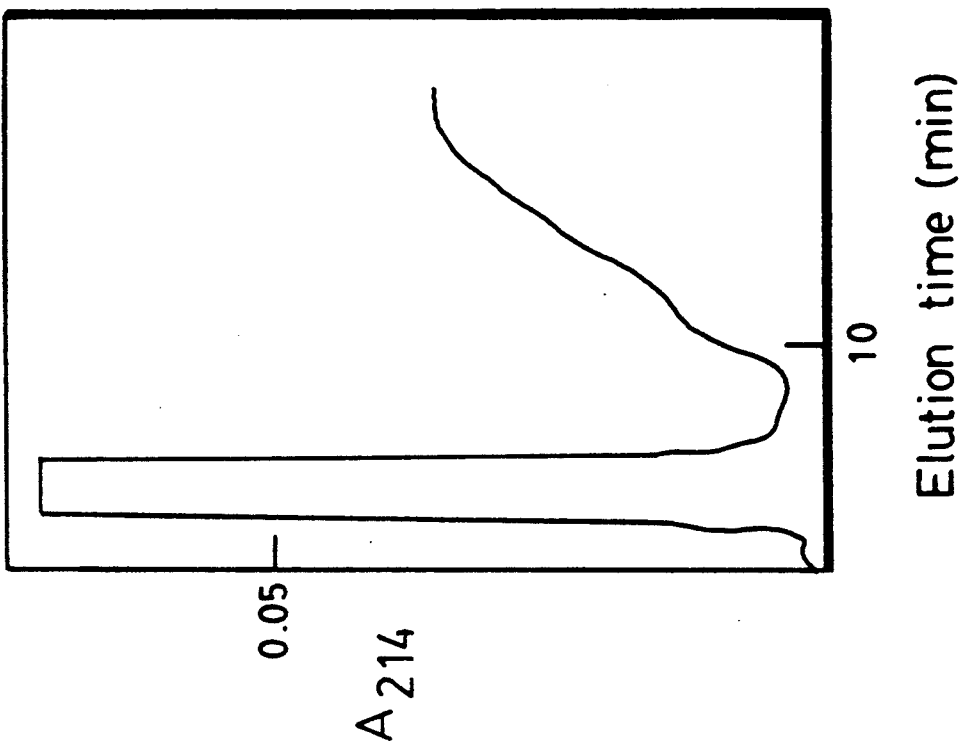
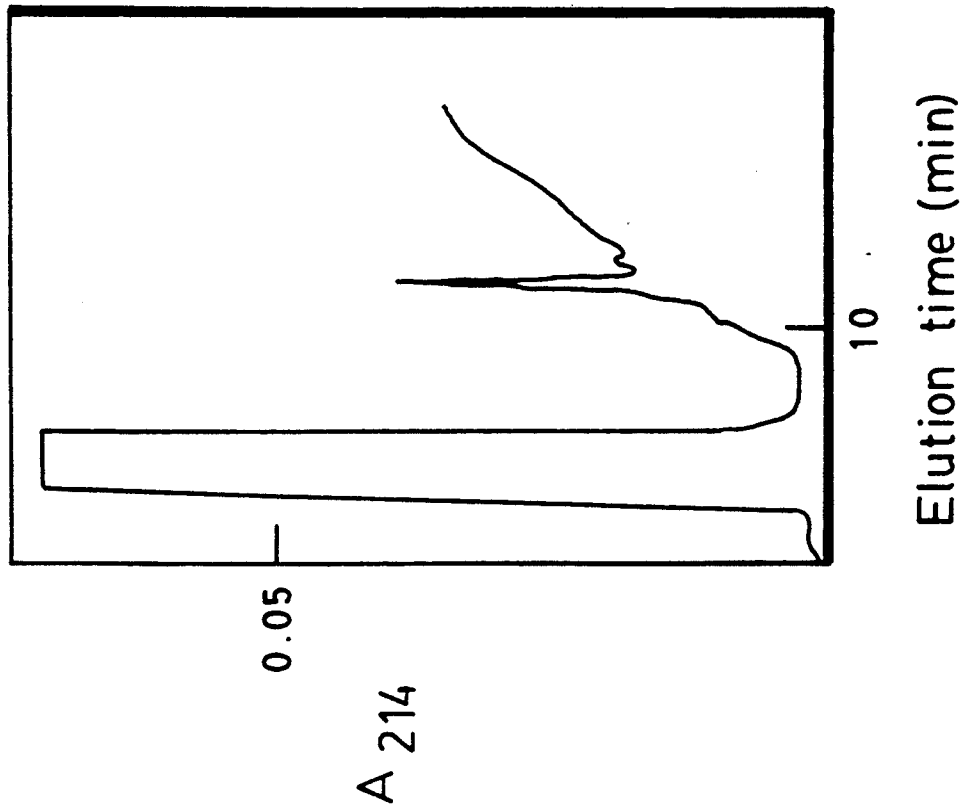

FIG. 3A

```
         10         20         30         40         50
CGGGGTGTCGACACGTTCAACCCGTTCTGCTGGCTCGAGAACGAAGTAG 60         70         80         90        100
GCCGTCTCGCTCTGGGTCTTCCAGGCCCGGACCGTCCGCCAGTCGTCCCG 110        120        130        140        150
AGGCCACTCTTCACCTCCACCATGAGCCTGGACATCCAGAGCCTGGACAT
                        MetSerLeuAspIleGlnSerLeuAspIl 160        170        180        190        200
CCAGTGTGAGGAGCTGAGCGACGCTAGAGCGGCCGAGCTCCTCCCTCTGC
eGlnCysGluGluLeuSerAspAlaArgTrpAlaGluLeuLeuProLeuL 210        220        230        240        250
TCCAGCAGTGCCAAGTGGTCAGGCTGGACGACTGTGGCCTCACGGAAGCA
euGlnGlnCysGlnValValArgLeuAspAspCysGlyLeuThrGluAla 260        270        280        290        300
CGGTGCAAGGACATCAGCTCTGCACTTCGAGTCAACCCTGCACTGGCAGA
ArgCysLysAspIleSerSerAlaLeuArgValAsnProAlaLeuAlaGl
```

FIG. 3B

```
           310       320       330       340       350
         GCTCAACCTGGCGCAGCAACGAGCTGGGCGATGTCGGCGTTGCATTGCCGTGC
         uLeuAsnLeuArgSerAsnGluLeuGlyAspValGlyValHisCysValL 360       370       380       390       400
         TCCAGGCCTGCAGACCCCTCCTGCAAGATCCAGAGCTGAGCTCCAG
         euGlnGlyLeuGlnThrProSerCysLysIleGlnLysLeuSerLeuGln 410       420       430       440       450
         AACTGCTGCCTGACGGGCCGGCTGCGGGTCCTGTCCAGCACACTACG
         AsnCysCysLeuThrGlyAlaGlyCysGlyValLeuSerSerThrLeuAr 460       470       480       490       500
         CACCCTGCCCACCCTGCAGGAGCTGCACCTCAGCGACAACCTCTTGGGGG
         gThrLeuProThrLeuGlnGluLeuHisLeuSerAspAsnLeuLeuGlyA 510       520       530       540       550
         ATGCGGGCCTGCAGCTGCTCTGCGAAGGACTCCTGGACCCCCAGTGCCGC
         spAlaGlyLeuGlnLeuLeuCysGluGlyLeuLeuAspProGlnCysArg 560       570       580       590       600
         CTGGAAAAGCTGCAGCTGGAGTATTGCAGCCTCTCGGCTGCCAGCTGCGA
         LeuGluLysLeuGlnLeuGluTyrCysSerLeuSerAlaAlaSerCysGl
```

FIG. 3C

```
       610       620       630       640       650
GCCCCTGGCCTCCGTGCTCAGGGCCAAGGCCGGACTTCAAGGAGCTCACGG
uProLeuAlaSerValLeuArgAlaLysProAspPheLysGluLeuThrV 660       670       680       690       700
TTAGCAACAACGACATCAATGAGGCTGGCCGTCCGTGTGTGCCAGGGC
alSerAsnAsnAspIleAsnGluAlaGlyValArgValLeuCysGlnGly 710       720       730       740       750
CTGAAGGACTCCCCCTGCCAGCTGGAGGCGCTCAAGCTGGAGAGCTGCGG
LeuLysAspSerProCysGlnLeuGluAlaLeuLysLeuGluSerCysGl 760       770       780       790       800
TGTGACATCAGACAACTGCCGGGACCTGTGCGGCATTGTGCCCTCCAAGG
yValThrSerAspAsnCysArgAspLeuCysGlyIleValAlaSerLysA 810       820       830       840       850
CCTCGCTGCGGGAGCTGGCCCTGGCCAGCAACAAGCTGGGTGATGTGGGC
laSerLeuArgGluLeuAlaLeuAlaLeuGlySerAsnLysLeuGlyAspValGly 860       870       880       890       900
ATGGCGGAGCTGTGCCCAGGCTGCTCCACCCAGCTCCAGGCTCAGGAC
MetAlaGluLeuCysProGlyLeuLeuHisProSerSerArgLeuArgTh
```

FIG. 3D

```
        910          920          930          940          950
CCTGTGGATCTGGGAGTGTGGCATCACTGCCAAGGGCTGCGGGGATCTGT
rLeuTrpIleTrpGluCysGlyIleThrAlaLysGlyCysGlyAspLeuC 960          970          980          990         1000
GCCGTGTCCTCAGGGCCAAGGAGACCTGAAGGAGCTCAGCCTGGCCGGC
ysArgValLeuArgAlaLysGluSerLeuLysGluLeuSerLeuAlaGly 1010         1020         1030         1040         1050
AACGAGCTGGGGGATGAGGGTGCCCGACTGCTGTGTGAGACCCTGCTGGA
AsnGluLeuGlyAspGluGlyAlaArgLeuLeuCysGluThrLeuLeuGl 1060         1070         1080         1090         1100
ACCTGGCTGCCAGCTGCTGGAGTCGCTGGTGAAGTCCTGCAGCTTCACAG
uProGlyCysGlnLeuLeuGluSerLeuTrpValLysSerCysSerPheThrA 1110         1120         1130         1140         1150
CCGCCTGCTGCTCCCACTTCAGCTCAGTGCTGGCCCCAGAACAGGTTTCTC
laAlaCysCysSerHisPheSerSerValLeuAlaGlnAsnArgPheLeu 1160         1170         1180         1190         1200
CTGGAGCTACAGATAAGCAACAACAGGCTGGAGGATGCGGGGCGTGCGGGA
LeuGluLeuGlnIleSerAsnAsnArgLeuGluAspAlaGlyValArgGl
```

FIG. 3E

```
          1210       1220       1230       1240       1250
GCTGTGCCAGGGCCTGGGCCAGCCTGGCTGCTGTGCTGTGCTGTGCTGGT
uLeuCysGlnGlyLeuGlyLeuGlyGlnProGlySerValLeuArgValLeuTrpL 1260       1270       1280       1290       1300
TGGCCGACTGCGATGTGAGTGACAGCAGCAGCTGCAGCAGCCTCGCCAACC
euAlaAspCysAspValSerAspSerSerCysSerSerLeuAlaAlaThr 1310       1320       1330       1340       1350
CTGTTGGCCAACCACACAGCCTGGCTGGACCTCAGCAACAACAACTGCCT
LeuLeuAlaAsnHisSerLeuArgGluLeuAspLeuSerAsnAsnCysLe 1360       1370       1380       1390       1400
GGGGACGCCCGGCATCCTGCAGCTGGTGGAGAGCGTCCGCCAGCCGGGCT
uGlyAspAlaGlyIleLeuGlnLeuValGluSerValArgGlnProGlyC 1410       1420       1430       1440       1450
GCCTCCTGGAGCAGCTGGTCCTGTACGACATTACTGGTCTGAGGAGATG
ysLeuLeuGluGlnLeuValLeuTyrAspIleTyrTrpSerGluGluMet 1460       1470       1480       1490       1500
GAGGACCGGGCTGCAGGCCCTGGAGAAGGACAAGCCATCCCTGAGGGTCAT
GluAspArgLeuGlnAlaLeuGluLysAspLysProSerLeuArgValIl
```

FIG. 3F

```
        1510      1520      1530      1540      1550
CTCCTGAGGCTCTCTTCCTGCTGCTGCTCTCCCTGGACGACCGGCCTCGAGG
eSerEnd 1560      1570      1580      1590      1600
CAACCCTGGGGCCCACCAGCCCCTGCCATGCTCTCACCCTGCATATCCTA 1610      1620      1630      1640      1650
GGTTTGAAGAGAAACGCTCAGATCCGCTTATTTCTGCCAGTATATTTTGG 1660      1670      1680      1690
ACACTTTATAATCATTAAAGCACTTTCTTGGCAAAAAAAAAA
```

INHIBITORS OF ANGIOGENIN

This is a continuation of application Ser. No. 07/177,942, filed Apr. 5, 1988, now U.S. Pat. No. 5,019,556, which is a continuation-in-part of application Ser. No. 07/038,008, filed Apr. 14, 1987, now U.S. Pat. No. 4,966,964, which is a continuation-in-part of application Ser. No. 07/038,250 filed Apr. 14, 1987, now abandoned.

BACKGROUND OF THE INVENTION

This is a continuation-in-part of our earlier applications U.S. Ser. No. 038,008, and U.S. Ser. No. 038,250, each of which was filed Apr. 14, 1987, and is hereby incorporated by reference.

Angiogenin is a human protein which induces blood vessel formation (Fett et al., 24 *Biochemistry* 5480, 1985). This biological activity is expressed with an amount as low as 35 fmol (using a chick embryo CAM assay procedure, Id.). Although originally isolated from medium conditioned by human tumor cells, angiogenin is not tumor specific, can be found in a variety of other cells and biological fluids, and most likely plays a role in normal and/or pathological neovascularization. It has a molecular weight of about 14,400 and an isoelectric point greater than about pH9.5, Id. Strydom et al. 24 *Biochemistry* 5486, 1985 also disclose the amino acid sequence of angiogenin.

Angiogenin is known to have an enzymatic activity. Specifically, it catalyzes limited cleavage of 28S and 18S rRNA to produce a specific pattern of products of 100–500 nucleotides in length (Shapiro et al., 25 *Biochemistry* 3727, 1986), but it has no significant ribonuclease activity in standard RNase assays, Id.

SUMMARY OF THE INVENTION

We have discovered that substances inhibiting at least the angiogenic activity of angiogenin can be used in methods and compositions for inhibiting tumor growth. Moreover, substances inhibiting the above described 18S, 28S rRNA-degrading enzymatic activity of angiogenin are effective tumor suppressants.

Accordingly, the invention features a method of inhibiting growth of a tumor in an animal, comprising administering an inhibitor of the angiogenic activity of angiogenin in sufficient quantity to inhibit the angiogenin activity in the tumor.

In a second aspect, the invention features a method of inhibiting growth of a tumor in an animal, comprising administering to the animal an inhibitor of the following specific enzymatic activity: cleavage of 18S or 28S rRNA to generally yield segments of 100 to 500 bases.

The following are features of preferred embodiments of the above methods: The inhibitor is able to bind to RNaseA or to angiogenin; the inhibitor is the complete natural molecule or segment or derivatives thereof having the ability to inhibit the above described enzymatic activity, and most preferably comprises a segment of a specific substance known as human placental RNase inhibitor (PRI) having the ability to inhibit the above described enzymatic activity of angiogenin; other proteins analogous to PRI from other human tissue or from other mammals also can be used; the inhibitor is administered at 10–10,000 µg/kg body weight of the animal; and the animal is a human.

In a third aspect, the invention features an inhibitor capable of inhibiting the angiogenic activity of angiogenin, wherein the inhibitor is dispersed within a medium that is physiologically compatible—i.e., suitable for administration to an animal—at a suitable concentration and in sufficient quantity to inhibit the angiogenic activity of naturally occurring angiogenin within at least a defined area of the animal, for example, the area immediately surrounding a tumor.

In preferred embodiments of this aspect, the inhibitor inhibits the enzymatic activity of angiogenin; and most preferably the inhibitor comprises a segment of PRI (or an analogous protein from other human tissue or from mammalian tissue) having the ability to inhibit the 18S, 28S rRNA-degrading activity described above.

In a fourth aspect, the invention features a method of inhibiting disorders associated with neovascularization. The method comprises administering to an animal an inhibitor of the angiogenic activity of angiogenin in sufficient quantity to inhibit angiogenic activity associated with the disorder.

In a fifth aspect, the invention features a therapeutic composition comprising a polypeptide comprising the amino acid sequence Val-Asn-Pro-Ala-Leu-Ala-Glu-Leu-(Asn-Leu Arg), Ser-Asn-Glu-Leu-Gly-Asp-Val-Gly, or Trp or Val-Leu-Trp-Leu-Ala-Asp-(Gln or Cys)-Asp-(Lys or Val). In preferred embodiments, a segment of the polypeptide has angiogenin inhibiting activity.

In a sixth aspect, the invention features engineered nucleic acid encoding the above amino acid sequences. Engineered nucleic acid is defined below, briefly it refers to any nucleic acid removed from its natural environment.

In a seventh aspect, the invention features engineered nucleic acid encoding a segment of a polypeptide having angiogenin inhibitory activity. Preferably, the nucleic acid is obtained by screening a mammalian gene library with a probe corresponding to a segment of a polypeptide having angiogenin inhibitory activity; the gene library comprises genomic or cDNA; the polypeptide is human placental ribonuclease inhibitor; the library comprises human DNA, or human cDNA; and the segment is Val—Asn—Pro—Ala—Leu—Ala—Glu—Leu—(Asn—Leu—Arg), Ser—Asn—Glu—Leu—Gly—Asp—Val—Gly, or (Trp or Val)

—Leu—Trp—Leu—Ala—Asp—(Gln or Cys)—Asp—(Lys or Val).

In an eighth aspect, the invention features a method for making a polypeptide having angiogenin inhibitory activity. The method comprises expressing engineered nucleic acid encoding the polypeptide in a host cell. Preferably, the polypeptide is a segment of human placental ribonuclease inhibitor.

This invention provides a means for preventing or reducing growth of tumors. The preferred inhibitor, PRI, is active when present in a slight molar excess over angiogenin and other PRI-binding proteins in the body fluids, or within a specified local area, such as that area immediately surrounding a tumor, and thus need only be provided at very low concentrations.

Other features and advantages of the invention will be apparent from the following description of the preferred embodiments thereof and from the claims.

DESCRIPTION OF THE PREFERRED EMBODIMENTS

The Figures will first briefly be described:

DRAWINGS

FIG. 1 is a graphical representation of the effect of angiogenin on inhibition of RNaseA activity toward uridylyl (3', 5') adenosine (UpA) by PRI (Blackburn, 254 J. Biol. Chem. 13484, 1979) as an example of an angiogenin inhibitor.

FIGS. 2A and 2B are a graphical representation of elution of angiogenin (A) or angiogenin and PRI (B) from an HPLC column.

FIGS. 3A–3F show the nucleotide sequence of PRI cDNA and the translated amino acid sequence.

STRUCTURE

Angiogenin

Figure 1:
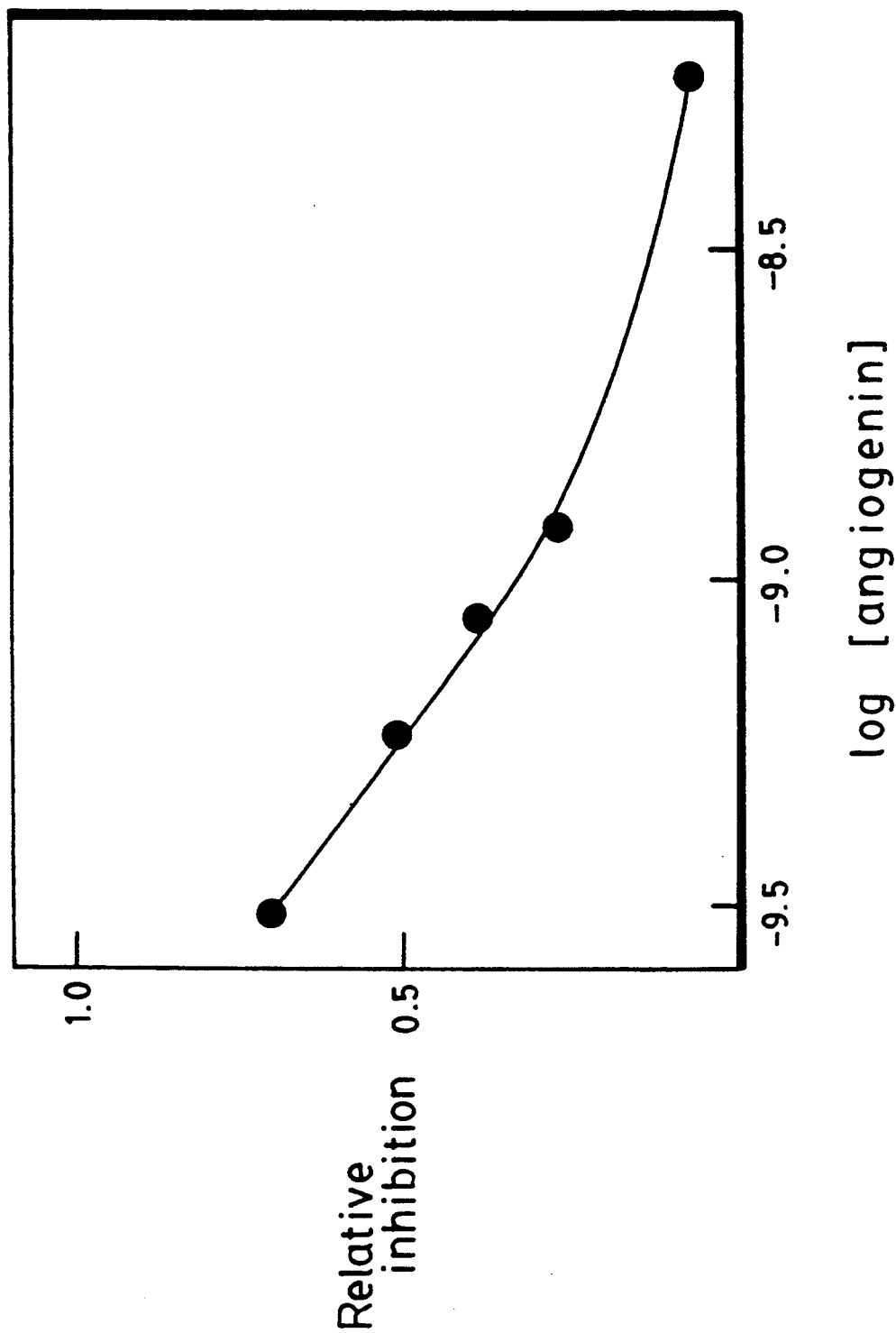

Angiogenin is a protein, having activities as described above, which can be obtained and purified as described by Fett et al., supra, and Shapiro et al., supra. Alternatively, angiogenin can be obtained and purified using recombinant DNA techniques. Kurachi et al., 24 Biochemistry 5494, 1985, describe the cDNA and gene encoding for angiogenin; this cDNA or gene can be expressed from a standard expression vector and the resulting angiogenin protein purified by standard procedure, e.g., in mammalian, yeast or various microbial expression systems. Id. at 5498.

Angiogenin Inhibitors

An angiogenin inhibitor is any compound able to inhibit the angiogenic activity of angiogenin. Preferably the inhibitor of angiogenin is a protein; most preferably it is a protein capable of binding to angiogenin and of inhibiting at least its biological angiogenic activity and preferably also its enzymatic 28S/18S rRNA-degrading activity. (The enzymatic activity is measured as described by Shapiro et al., 20 pra. Briefly, 15–20 µg RNA is incubated with about 1.9 µM angiogenin at 37° C. in either 30 mM Hepes or 20 mm Tris, pH 7.5, containing 30 mM NaCl in a total volume of 13.5 µl. The reaction is terminated after about 90 minutes using 48 µl of a formamide/formaldehyde reagent, Id.) Preferably, the inhibitor is isolated from mammalian tissues, most preferably from human placental tissue.

One example of the inhibitor, PRI, can be isolated as described by Blackburn (254 J.Biol.Chem. 12,484, 1979). Proteins which are substantially equivalent to PRI, that is they have similar amino acid compositions, and have similar biological and enzymatic inhibitory activities, can be found not only in other human tissues but in other mammalian tissues. For example, the various inhibitors of RNAse A described by Burton et al., (19 Int. J. Peptide Protein Res. 372, 1982, hereby incorporated by reference) may be suitable in this invention. These proteins have about 70–80% similarity in amino acid composition to PRI, as shown in Table 1 (taken from Burton et al., Id.). Such proteins are also angiogenin inhibitors for purposes of the invention. Methods for isolating and purifying these proteins are given below, using standard affinity chromatography methodology, or recombinant DNA techniques.

TABLE 1

Amino acid compositions of various liver RNase inhibitors and human placental RNase inhibitor

| | Residues/molecule of inhibitor | | | | | |
|---|---|---|---|---|---|---|
| | Liver | | | | | Placenta |
| Amino acid | Beef | Mouse | Pig | Rat | Sheep | Human |
| Asx | 47 | 55 | 47 | 59 | 48 | 47 |
| Threonine | 21 | 22 | 25 | 23 | 19 | 16 |
| Serine | 45 | 43 | 43 | 43 | 42 | 45 |
| Glx | 62 | 63 | 64 | 60 | 62 | 64 |
| Proline | 15 | 16 | 15 | 17 | 17 | 17 |
| Glycine | 47 | 33 | 43 | 33 | 51 | 36 |
| Alanine | 37 | 30 | 35 | 29 | 35 | 34 |
| Valine | 24 | 20 | 19 | 22 | 23 | 24 |
| Methionine | 2 | 3 | 2 | 2 | 1–2 | 2–3 |
| Isoleueine | 9 | 3 | 9 | 10 | 10 | 12 |
| Leucine | 91 | 94 | 93 | 89 | 92 | 85 |
| Tyrosine | 5 | 5 | 4 | 5 | 4 | 4 |
| Phenylalanine | 4 | 3 | 2 | 5 | 4 | 6 |
| Histidine | 6 | 3 | 9 | 6 | 5 | 6 |
| Lysine | 14 | 21 | 15 | 20 | 15 | 17 |
| Arginine | 19 | 19 | 21 | 20 | 20 | 23 |
| ½ Cystime + cysteine | 30 | 26–27 | 35 | 31 | 27 | 30 |
| Tryptophan | 5 | 5 | 5 | 5 | 6 | 5 |
| Total residues | 483 | 475 | 486 | 479 | 482 | 473 |

Alternatively, the gene encoding an inhibitor may be cloned by standard techniques. Such techniques include purifying the inhibitor, determining part of its amino acid sequence, creating a DNA probe capable of coding for this amino acid sequence, and using the probe to detect recombinant vectors in a cDNA or genomic library created from, e.g., placental cells. The cloned gene can then be expressed in any suitable expression vector in a suitable expression host cell, e.g., bacteria, yeast, or tissue culture cells. The recombinant inhibitor protein produced by those cells can then be purified from the culture supernatant or from the cells.

Suitable oligonucleotide probes for detecting clones expressing polypeptides according to the invention can be generated from the nucleic acid sequence given in FIG. 3. using, e.g., fragments of the FIG. 3 sequence (or the corresponding antisense sequence) that are at least 10, and preferably at least 16 bases in length. Probes with minor modifications (e.g. deviation at less than 3 of 16 positions) of the FIG. 3 sequence are acceptable. The following fragments are provided by way of example only; the corresponding antisense strands would be operative also:

5'-TGGCTGTGGCTGGCCGACCAGGAGAA-3'

5'-GTGCTCTGGTTGGCCGACTGCGAT-3'

5'-GTGAACCCTGCCCTGGCTGA-3'

5'-GTGAACCCTGGACTGGCAGA-3'

5'-AATGAGCTGGGCGATGTGGG-3'

5'-AACGAGCTGGGCGATGTCGG-3'

More generalized strands and corresponding antisense strands are:

5'-TGGBTNTGGBTNGCNGABCADGABAA-3'
5'-TTI TCBTGI TCCGCCAI CCACTI CCA-3'
       I       I       I

-continued
5'-AABGADBTNGGNGABGTNGG-3'
5'-CCCACI TCCCCCAI BTCI TT-3'
      I      I  I

5'-GTNAABCCNGCNGT NGCNGA-3'
5'-TCCGCCAI CGCCGGI TTCAC-3'
       I

In each of the above sequences B is C or T; I is inosine (which can base pair with A, T, or C) N is A, T, C or G, and

C
I is C or I.

Inosine is used in the probe sequence in place of A, T, and C so that the number of probes to be synthesized as a mixture can be minimized without prejudicing their hybridizing ability to the natural gene or cDNA sequences.

One example of a method to isolate a cDNA clone of the gene encoding PRI is to use the above three antisense strand oligonucleotide probes under strigent hybridization conditions to probe a cDNA library of human placental DNA.

Another example of a procedure for isolating and screening cDNA clones expressing PRI is as follows. Antibodies are raised in rabbits against PRI purified as described above. The antibodies are purified by affinity chromatography, using PRI coupled to an activated solid matrix such as Sepharose (e.g. activated by CNBr).

Any clones which hybridize to one or more of the probes, and preferably hybridize to all three, or any clones that express proteins that bind to anti-PRI antibodies, are potential clones of the PRI-encoding gene. To determine whether the clones do encode PRI, they can be purified, followed by re-checking of re-hybridization with the probes or of expression of proteins that bind anti-PRI antibodies.

Ultimately, the clones can be sequenced and the sequences compared to see if they correlate with the known properties of PRI, i.e., the amino acid sequence, molecular weight and amino acid composition. Expression of PRI can then be achieved by insertion of the cDNA clone into an expression vector and the recombinant PRI which is expressed, isolated, and purified. All such clones contain engineered DNA, that is, DNA taken from its natural environment and inserted into a vector, such as a plasmid or phage, or even within the genome of an organism. Thus, the engineered DNA is no longer surrounded by naturally occuring sequences on either side of it. Generally such engineered DNA is constructed using recombinant DNA techniques, and does not include naturally occurring DNA in which, for example, a translocation of chromosomal DNA in vivo has changed the environment of DNA; however it does include such natural events which occur after the DNA has been manipulated in some way by recombinant DNA methodology.

We have determined the nucleotide sequence of human PRI cDNA and the amino acid sequence of human PRI inferred from that nucleotide sequence. We have confirmed a portion of that amino acid sequence by Edman degradation of PRI tryptic peptides.

FIG. 3 shows the PRI cDNA sequence and translated amino acid sequence. A bacterium, *E. coli* DH5α, transformed with vector pUC18-PRI(A) containing the cDNA of FIG. 3 has been deposited with the American Type Culture Collection in Maryland under access number 67668 on Mar. 31, 1988.

Angiogenin inhibitors can be obtained using the PRI information in FIG. 3, e.g., by producing recombinant PRI inhibitor using standard techniques for culturing cells that include the PRI cDNA on a suitable expression vector, and purifying the PRI from the culture supernatant.

Fragments and variants of the PRI of FIG. 3 sequence are also suitable. For example. PRI can be fragmented (e.g. by tryptic digestion) and the resulting fragments (purified by HPLC) can be assayed as described elsewhere in this application for angiogenin inhibitory activity. Specific PRI fragments of use are as follows:

Val—Asn—Pro—Ala—Leu—Ala—Glu—Leu—Asn—Leu—Arg;
Ser—Asn—Glu—Leu—Gly—Asp—Val—Gly;
(Trp or Val)—Leu—Trp—Leu—Ala—Asp—(Cys or Gln)—Asp—(Val or Lys).

PRI from other mammals, such as the ones shown in Table 1, can be obtained and analyzed by cloning them from other mammals and providing angiogenic fragments as described above.

Once cloned, the naturally occurring gene may also be modified by standard techniques, for example, by altering the amino acid sequence of the inhibitor, so long as the inhibitor retains the ability to inhibit the biological angiogenic activity of angiogenin. Such alterations may be designed to increase the binding ability of the inhibitor for angiogenin. Further, related inhibitor-encoding genes can be isolated by using a part of the above described cloned gene encoding an inhibitor as a probe for libraries, constructed by standard techniques, of other animal genomes.

In order to isolate other inhibitors, one possible procedure includes detecting proteins able to bind angiogenin, for example, by binding angiogenin to a column and passing a sample containing potential inhibitor proteins through this column. (RNaseA can be used in place of angiogenin, as described by Blackburn 254 *J. Biol. Chem.* 12488, 1979.) Bound protein can then be eluted, for example, by using 0.1M sodium acetate pH 5.0 containing 3M NaCl, 15% glycerol, 1 mM EDTA and 5 mM DTT, which is able to dissociate the angiogenin-/inhibitor complex. The eluted protein can then be purified and tested, as described below, to see if the released proteins inhibit the angiogenic activity of angiogenin, or altenatively if they inhibit its enzymatic activity. The active protein(s) may then be purified by standard procedure.

Further, it is possible to use segments of inhibitors, such as segments of PRI, which retain the biological inhibiting character of the native inhibitor. Such segments can be created by standard procedure using proteases to digest natural inhibitors to produce active segments; or by using recombinant DNA techniques to remove non essential parts of the structural gene or cDNA encoding the inhibitor, and then expressing this engineered DNA to produce a modified inhibitor.

INHIBITORY ACTIVITY

Below is an example of in vitro measurements relative to the inhibitory effect of PRI on angiogenin. This example is not meant to be limiting for the invention and those skilled in the art will realize that these examples are indicative of whether other inhibitors or segments thereof can be used in the methods described below.

MEASUREMENT OF INHIBITION OF THE ENZYMATIC ACTIVITY OF ANGIOGENIN

Angiogenin and PRI were purified generally as described by Fett et al. and Shapiro et al., cited above. The enzymatic activity of angiogenin was measured as described by Shapiro et al., supra. Briefly, angiogenin catalyzes the cleavage of 28S and 18S rRNA to form products of 100 to 500 nucleotides in length. These products are stable and include a large, approximately 500 bases, segment which is visible in an agarose gel. In one experiment, 12 μg of RNA was incubated with or without angiogenin and/or PRI at 37° C. in 33 mM Hepes, and 33 mM NaCl, pH7.5. After 30 min the reaction was terminated, as described by Shapiro et al., supra, the samples run on a 1.1% agarose gel, and stained with ethidium bromide. 0.96 μM PRI completely inhibited the enzymatic degradation of rRNA by 0.8 μM angiogenin. PRI alone had no activity on rRNA. Thus, PRI is a potent inhibitor of the enzymatic activity of angiogenin, being active at only just over a 1:1 ratio with angiogenin.

STABILITY OF THE ANGIOGENIN/PRI COMPLEX

For therapeutic use of the angiogenin inhibitor it is advantageous to use an inhibitor that binds strongly to angiogenin and reduces its biological activity. PRI is such an inhibitor.

RNaseA also binds to PRI and competes with angiogenin for binding PRI in solution. The enzymatic activity of RNaseA is also inhibited by PRI. These properties can be used to determine the stability of the PRI-/angiogenin complex, as follows.

UpA is an excellent substrate for RNaseA but not for angiogenin. In one experiment, a varying amount of angiogenin was added to a mixture of 0.27 nM RNaseA and 0.20 nM PRI, with the RNaseA and angiogenin being mixed together first, followed by PRI for 5 min. at 25° C., and then the UpA substrate (0.2 mM, in a buffer of 10 μg/ml human serum albumin (HSA), 0.1M 2-(N-morpholino)-ethane-sulfonic acid, 0.1M NaCl, and 1 mM EDTA pH6.0). The more angiogenin present in the mixture the more PRI that will be bound to it, and thus the less PRI that will be bound to RNaseA and able to inhibit its enzymatic activity. Further, the stronger the binding of PRI to angiogenin than to RNaseA, the greater the reduction in inhibition of RNaseA activity, since PRI will then preferentially bind to angiogenin. The results are shown in FIG. 1. Relative inhibition is calculated as (Vo-Va)/(Vo-Vr) where Vo denotes velocity of RNaseA activity in the absence of PRI, Vr denotes velocity in the presence of PRI with no angiogenin added, and Va is velocity in the presence of PRI with angiogenin added. At 5.8 nM angiogenin there is essentially no inhibition of RNaseA activity. Thus, a large excess of angiogenin is needed to remove all the PRI from reacting with and inhibiting the RNaseA.

In a related experiment, the $K_i$ for angiogenin and PRI can be estimated using the above method and modifying it so that the PRI and angiogenin are firstly preincubated for 10 minutes, followed by addition of RNaseA and UpA. This assay determines the level of free inhibitor remaining after incubation of PRI and angiogenin. Thus, if the dissociation of PRI and angiogenin is slow there will be little inhibition of RNaseA activity. At a ratio of angiogenin:PRI of 1:1.2 no free PRI was detected. Thus, PRI and angiogenin are tightly bound and appear to have a $K_i$ less than 0.1 nM.

The strength of binding of PRI and angiogenin was also demonstrated by cation-exchanqe HPLC. This process can distinguish free angiogenin from angiogenin/PRI complex. A Synchropak CM 300 column (250×4.1 mm; Sychrom, Inc.), a Waters Associates liquid chromatography system and a Hewlett-Packard 3390A integrator were used; the results are shown in FIG. 2. Samples of 1 ml in 0.1M Tris, pH7, containing 1 mM EDTA and 10 μg HSA were eluted with a 10 min. linear gradient from 220–620 mM NaCl in 20 mM sodium phosphate, pH7, at a flow rate of 1 ml/min.; effluents were monitored at 214 nm. In panel A is shown elution of 0.64 μg angiogenin; in panel B the elution of 0.64 μg angiogenin and 12 μg PRI. There is no detectable free angiogenin shown in panel B. Addition of RNaseA to the angiogenin - PRI mixture at 32-fold excess did not produce free angiogenin, even after 17 h incubation. Thus, dissociation of angiogenin/PRI appears to have a half life of greater than 1 day.

INHIBITION OF ANGIOGENIC ACTIVITY

Angiogenesis (i.e., angiogenic activity) was assessed by a modification of the chick embryo chorioallantoic membrane (CAM) assay of Knighton et al. 35 Brit.J.-Cancer 347 (1977) described by Fett et al., supra. For this assay PRI was desalted using an Amicon Centricon-10 microconcentrator to dilute the buffer at least 500 fold. This removes interfering components, from the PRI solution, which may adversely affect the experiment or may harm the egg itself. The results of adding PRI to the angiogenin are shown in Table 2 below.

Data for experiments #1 and #2 represent composites of results obtained in 2 and 3 sets of assays, respectively. Between 10 and 20 eggs were utilized for each of the three experimental groups within each set. The following amounts of angiogenin and PRI were employed: Experiment #1, 75 ng and 2 μg, respectively; Experiment #2, 46 ng and 700 ng; and Experiment #3, 25 ng and 180 ng.

TABLE 2

| Sample | % Positives (Total Number of Eggs) Experiment | | |
|---|---|---|---|
|  | #1 | #2 | #3 |
| Angiogenin | 58 (24) | 52 (54) | 62 (13) |
| PRI | 17 (29) | 33 (48) | 17 (12) |
| Angiogenin + PRI | 15 (26) | 25 (52) | 7 (14) |

From these results it is evident that excess PRI decreases angiogenin activity to a level indistinguishable from that observed with the buffer and inhibitor alone controls.

INHIBITION OF TUMOR GROWTH

For immunotherapeutic studies, male nude (nu/nu) mice (Charles River Laboratories) were maintained under laminar flow conditions, and were age- and cage-matched (5 animals per cage) prior to experimentation. Experimental animals (5–10 per group) were injected subcutaneously (S.C.) with $5 \times 10^5$ HT-29 human colon adenocarcinoma cells (Fogh et al., In Human Tumor Cells In Vitro, pp115–160 ed. Fogh, Plenum Press, New York., 1975) on day 0. Also on day 0, animals were treated with either buffer control (the buffer used to store PRI dialysed against phosphate buffered saline; 0.2 g/l KCl, 0.2 g/l KH$_2$PO$_4$, 8 g/l NaCl and 2.16 g/l Na$_2$HPO$_4$.7H$_2$O, pH7.4 at 37° C., PBSA 100 μl) or placental inhibitor (100 μl) at varying dosages by S.C. or intraperitoneal (I.P.) injection. Treatment regimens included daily injections (10–11 doses) or injections at 2–3 day intervals (5–10 doses) depending on the experimental protocol. Assessment of animal health, weight, tumor size as well as photographic records were recorded 2–3 times per week. At the termination of the experiments blood and tissue samples were collected for immunological and histological evaluation.

In one experiment, forty male nu/nu mice were injected S.C. with 5×10$^5$ HT 29 cells on day 0. Additionally, on day 0 mice 1-10 (Group 1) received 100 μl of control buffer; mice 11-20 (Group 2) received 10 μg in 100 μl of placental inhibitor; mice 21-30 (Group 3) received 1.0 μg in 100 μl of placental inhibitor; and mice 31-40 received 0.1 μg in 100 μl of placental inhibitor. Groups 1 and 2 received further injections of buffer or 10 μg of placental inhibitor, respectively, on days 1, 4, 6, 8, 18, 20, and 22. On days 1, 4, 6 and 8, Groups 3 and 4 received placental inhibitor at dosages of 1.0 μg or 0.1 μg, respectively. All treatment injections were given I.P. After 60 days, only animals 13, 14, 17, 18, 20 and 24 remained tumor free. Thus, inocululation with 10 μg PRI prevented tumor formation in about 60% of animals.

Inhibition of both the biological and enzymatic activities of angiogenin by an inhibitor has important mechanistic, physiologic and pharmacologic implications. It is consistent with the hypothesis that these two actions of angiogenin are interrelated, as suggested previously by the simultaneous loss of both activities upon carboxymethylation by bromoacetate at pH 5 5. Shapiro et al., supra. Further it raises the possibility that such inhibitors may play a role in the in vivo regulation of angiogenin. The angiogenin/PRI interaction likely involves regions of angiogenin separated widely in the three-dimensional structure, many of them outside the active center. Thus, conservation of residues necessary for enzymatic activity alone probably cannot account for the strength of the interaction.

This implies that the capacity of angiogenin to bind PRI has been maintained independently during evolution. Apparently, binding by PRI and other inhibitors reflects a physiologically relevant control mechanism having pharmacologic and therapeutic potential. For example, as shown above, these inhibitors are active in prevention of tumor formation in mice. Apparently they are suitable for injection into humans or other animals in order to prevent tumor growth, and other diseases associated with neovascularization, e.g., diabetic retinopathy, rheumatoid arthritis, and Kaposi's sarcoma. That is, they are suitable for treating disorders where vascularization plays an important role in the pathophysiology of diseases such as solid tumors, hemangiomata and psoriasis.

Preferably, they are injected intravascularly, most preferably intravenously, or injected intraperitoneally in a physiologically compatible medium (such as PBSA, or those buffers and agents described by Krakoft, Ca-A Cancer Journal for Clinicians, March/April 1987, Vol. 37:93), suitable for administration to an animal in a sufficient quantity, e.g., about 10–10,000 μg/kg body weight of the animal, to inhibit naturally occuring biological activity of angiogenin within the animal. Alternatively, they can be administered topically to a specific area, or injected subcutaneously.

We have found that these inhibitors are stable for at least 2 weeks even at concentrations as low as 8 μM when they are in a purified form; there is no need to include DTT in the storage buffer or the therapeutic composition being administered, however, natural agents, which are physiologically compatible, e.g., N-acetyl cysteine or cysteine or cysteamine may be used. For administration it is important that the buffer fluid not injure the patient. It is possible that these inhibitors may be used prophylatically at a low concentration. Thus, for example, it is appropriate to administer 10–10,000 μg/kg body weight to patients at risk of cancer development, e.g., patients who have had a primary tumor removed.

Other embodiments are within the following claims.

We claim:

1. Nucleic acid encoding the amino acid sequence consisting essentially of:

Val—Asn—Pro—Ala—Leu—Ala—Glu—Leu—(Asn—Leu—Arg);
Ser—Asn—Glu—Leu—Gly—Asp—Val—Gly; or
(Trp or Val)—Leu—Trp—Leu—Ala—Asp—(Cys or Gln)—Asp—(Val or Lys).

* * * * *